(12) United States Patent
Antesberger et al.

(10) Patent No.: US 11,153,488 B2
(45) Date of Patent: Oct. 19, 2021

(54) VARIABLE LATENCY AND FRAME RATE CAMERA

(71) Applicant: United States of America, as represented by the Secretary of the Army, Fort Belvoir, VA (US)

(72) Inventors: Anthony Wayne Antesberger, Woodbridge, VA (US); William C. Cronk, Fredericksburg, VA (US)

(73) Assignee: UNITED STATES OF AMERICA, AS REPRESENTED BY THE SECRETARY OF THE ARMY, Washington, DC (US)

(*) Notice: Subject to any disclaimer, the term of this patent is extended or adjusted under 35 U.S.C. 154(b) by 0 days.

(21) Appl. No.: 16/914,658

(22) Filed: Jun. 29, 2020

(65) Prior Publication Data

US 2021/0099647 A1    Apr. 1, 2021

Related U.S. Application Data

(60) Provisional application No. 62/906,232, filed on Sep. 26, 2019.

(51) Int. Cl.
*H04N 5/232* (2006.01)
*G06F 3/01* (2006.01)
*H04N 5/33* (2006.01)

(52) U.S. Cl.
CPC ......... *H04N 5/23258* (2013.01); *G06F 3/017* (2013.01); *H04N 5/23229* (2013.01); *H04N 5/23267* (2013.01); *H04N 5/232933* (2018.08); *H04N 5/33* (2013.01)

(58) Field of Classification Search
CPC .......... H04N 5/23258; H04N 5/23267; H04N 5/232933; H04N 5/33; H04N 5/23229; G06F 3/017
See application file for complete search history.

(56) References Cited

U.S. PATENT DOCUMENTS

| | | | |
|---|---|---|---|
| 5,668,593 A | 9/1997 | Lareau et al. | |
| 2012/0105473 A1 | 5/2012 | Bar-Zeev et al. | |
| 2013/0201291 A1 | 8/2013 | Liu et al. | |
| 2015/0379772 A1* | 12/2015 | Hoffman | G06T 19/006 345/633 |
| 2016/0189429 A1* | 6/2016 | Mallinson | G02B 27/017 345/633 |
| 2017/0206673 A1* | 7/2017 | Kawamoto | G06F 1/163 |
| 2017/0318235 A1* | 11/2017 | Schneider | G06K 9/00664 |
| 2020/0051207 A1* | 2/2020 | Ogasawara | G06F 1/1686 |

* cited by examiner

*Primary Examiner* — Ahmed A Berhan
(74) *Attorney, Agent, or Firm* — Richard J. Kim

(57) ABSTRACT

An imaging system comprises an image sensor configured to detect images, an inertial measurement unit configured to measure movement of the image sensor, a display unit configured to display the images detected by the image sensor, and a control unit. The control unit is configured to control display of the images by the display unit based on the movement measured by the inertial measurement unit. An exemplary variable latency and frame rate camera embodiment is disclosed.

18 Claims, 5 Drawing Sheets

VARIABLE LATENCY AND FRAME RATE CAMERA

CROSS-REFERENCE TO RELATED APPLICATIONS

This application claims priority to U.S. Provisional Patent Application No. 62/906,232, filed on Sep. 26, 2019, the disclosure of which is incorporated herein by reference in its entirety.

GOVERNMENT INTEREST

The invention described herein may be manufactured, used, sold, imported, and/or licensed by or for the Government of the United States of America.

FIELD OF THE INVENTION

This invention relates to the automated control of an imaging system providing adjustment of performance in real time based on movement of the system.

BACKGROUND OF THE INVENTION

Imaging systems that collect and display image data can cause motion sickness in a human watching the images displayed if the imaging system is moving. This is particularly true for systems mounted on a user's head and/or body. One way to counter the motion sickness effect is to increase the frame rate of the imaging system and display. However, increasing the frame rate increases the power consumption. Accordingly, the present inventors invented an imaging system that avoids motion sickness while minimizing power consumption.

SUMMARY OF THE INVENTION

The present invention broadly comprises an apparatus and a method for controlling an imaging system.

In one embodiment, the apparatus includes an image sensor configured to detect images, an inertial measurement unit configured to measure movement of the image sensor, a display unit configured to display the images detected by the image sensor, and a control unit configured to control the display of the images by the display unit based on the movement measured by the inertial measurement unit.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION

Reference is presently made in detail to exemplary embodiments of the present subject matter, one or more examples of which are illustrated in or represented by the drawings. Each example is provided by way of explanation of the present subject matter, not limitation of the present subject matter. In fact, it will be apparent to those skilled in the art that various modifications and variations can be made in the present subject matter without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the disclosure and equivalents thereof.

Figure 1:
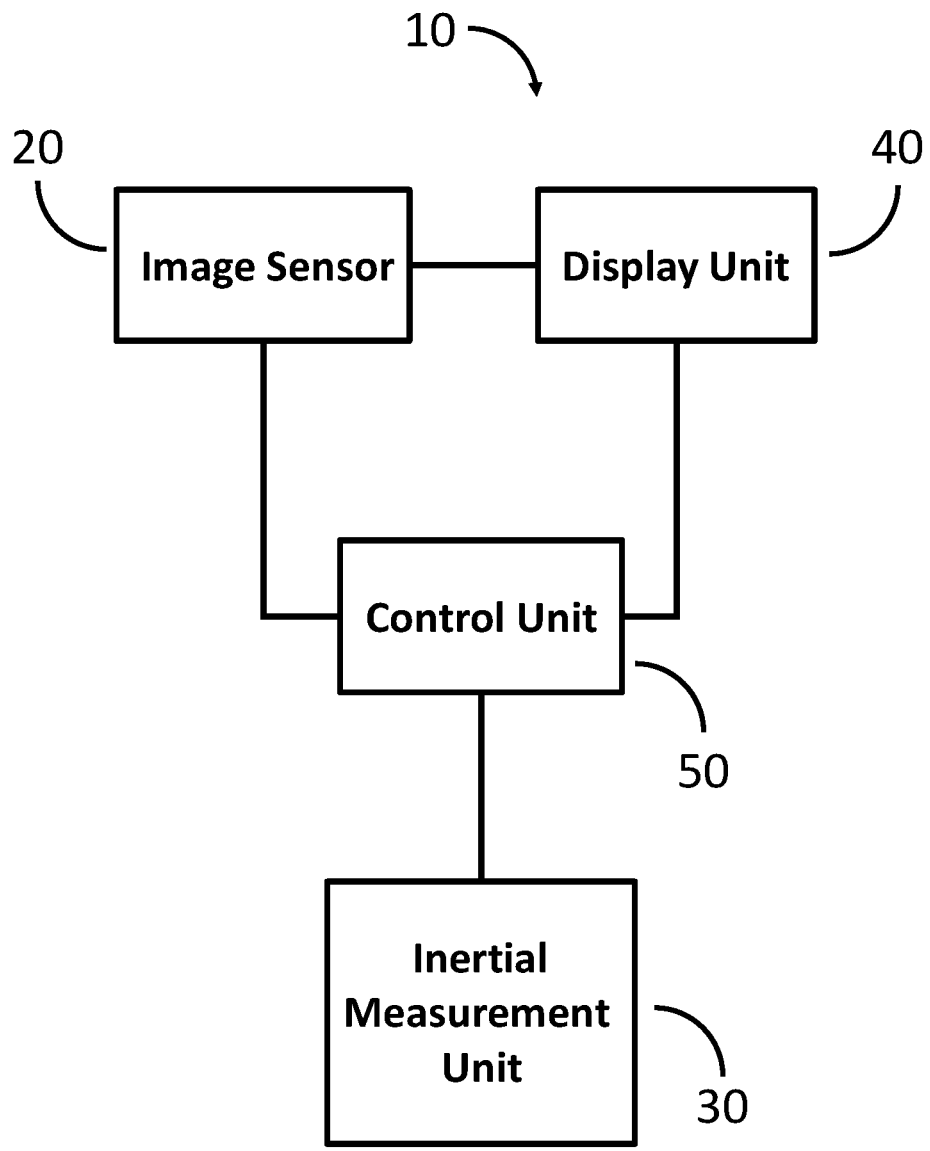
FIG. 1 illustrates a first embodiment of the present invention.
Figure 2:
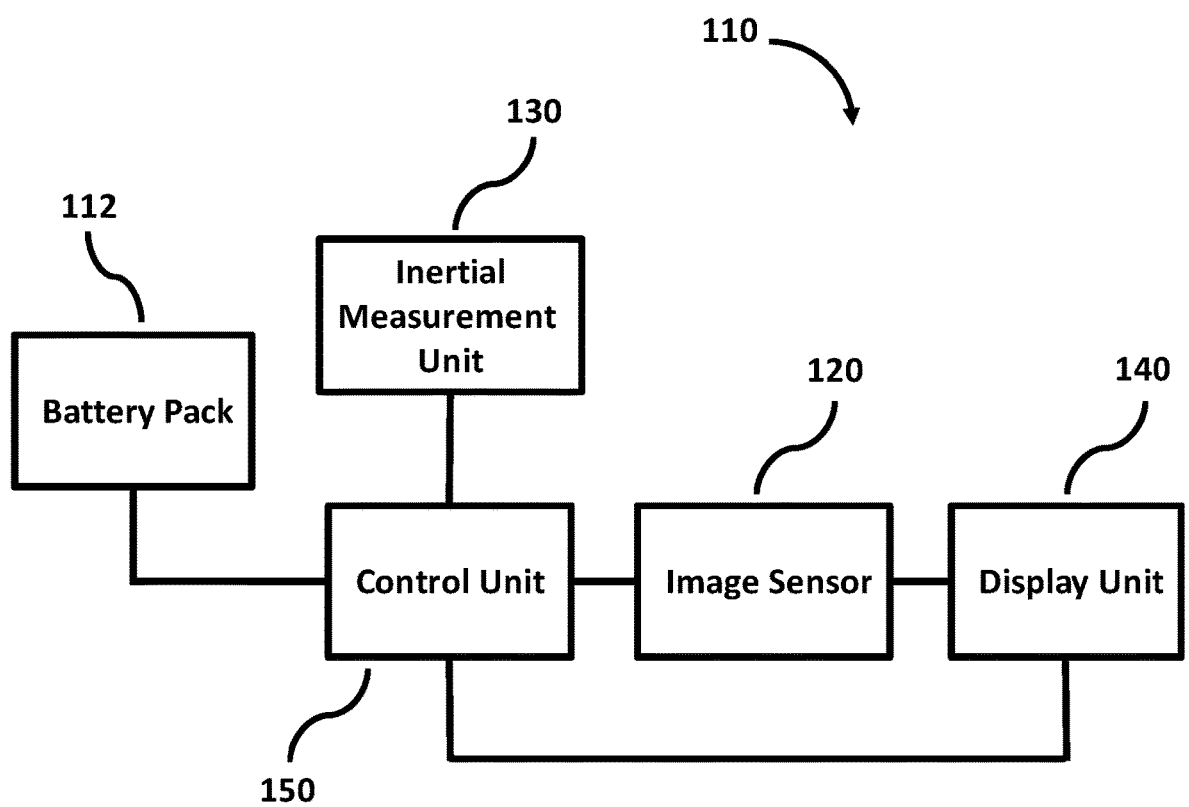
FIG. 2 illustrates a second embodiment of the present invention.

The invention broadly comprises an imaging and display system 10 (shown in FIG. 1), of which a specific embodiment is entitled the Variable Latency and Frame Rate Camera (VLFRC 110, shown in FIG. 2). VLFRC 110 utilizes an IMU module 130 to provide 3-axis angular velocity data (roll, pitch, and yaw rates), which are used to control features of VLFRC 110 in real-time. VLFRC 110 provides an image stream to the eye level display when helmet mounted. It has available multiple frame rates, a latency adjustment, exposure mode, manual gain, and manual level, and typical default values are set to help reduce power consumption. VLFRC 110 has modes adjusted based on multi axis angular velocity, as provided via the embedded IMU chipset (included in IMU 130), enabling features that assist to minimize motion sickness caused by sensory conflict while in motion, and then readjusting when not in motion to achieve minimum power consumption.

As noted above, first embodiment 10 of the present invention is illustrated in FIG. 1. Device 10 includes image sensor 20, Inertial Measurement Unit (IMU) 30, display unit 40, and control unit 50. Image sensor 20 collects image data based on, for example, visible light. In other embodiments, image sensor 20 collects near infrared (IR) data, short wave IR data, mid wave IR data, and/or long wave IR data. IMU 30 measures the amount of movement of the system, if any. Display unit 40 displays the image data collected by image sensor 20 on a display. Control unit 50 controls the image sensor 20 and display of the image data based on the movement measured by IMU 30. For example, control unit 50 may increase the frame rate of image sensor 20 and display unit 40, decrease the latency time of display unit 40, or both. Device 10 may be any imaging and display system that may undergo any movement that would cause motion artifacts in the displayed image. If motion artifacts in the image are severe enough, it may cause motion sickness in a human monitoring the image.

A second embodiment of the present invention is shown in FIG. 2, namely VLFRC 110. VLFRC 110 includes battery pack 112 and user button to power up the VLFRC 110. In an exemplary embodiment, control unit 150 includes a Field Programmable Gate Array (FPGA) & Micro controller assembly which initializes image sensor 120 with the last used timing configuration data which points to the last programmed set of configuration data to initialize with. In an exemplary embodiment, image sensor 120 includes a CMV2000 image sensor. The IMU 130 is powered on at the same time, and starts sending angular velocity data into control unit 150 for monitoring of angular velocities, and depending on the angular velocity status, control unit 150 will continue with the current configuration set or will change the configuration data set based on need to speed up or slow down the frame rate. The resulting image stream from image sensor 120 is fed into the display unit 140 for viewing by the user. In an exemplary embodiment, display unit 140 includes an EMA-10050x series micro display and eyepiece.

Figure 5:
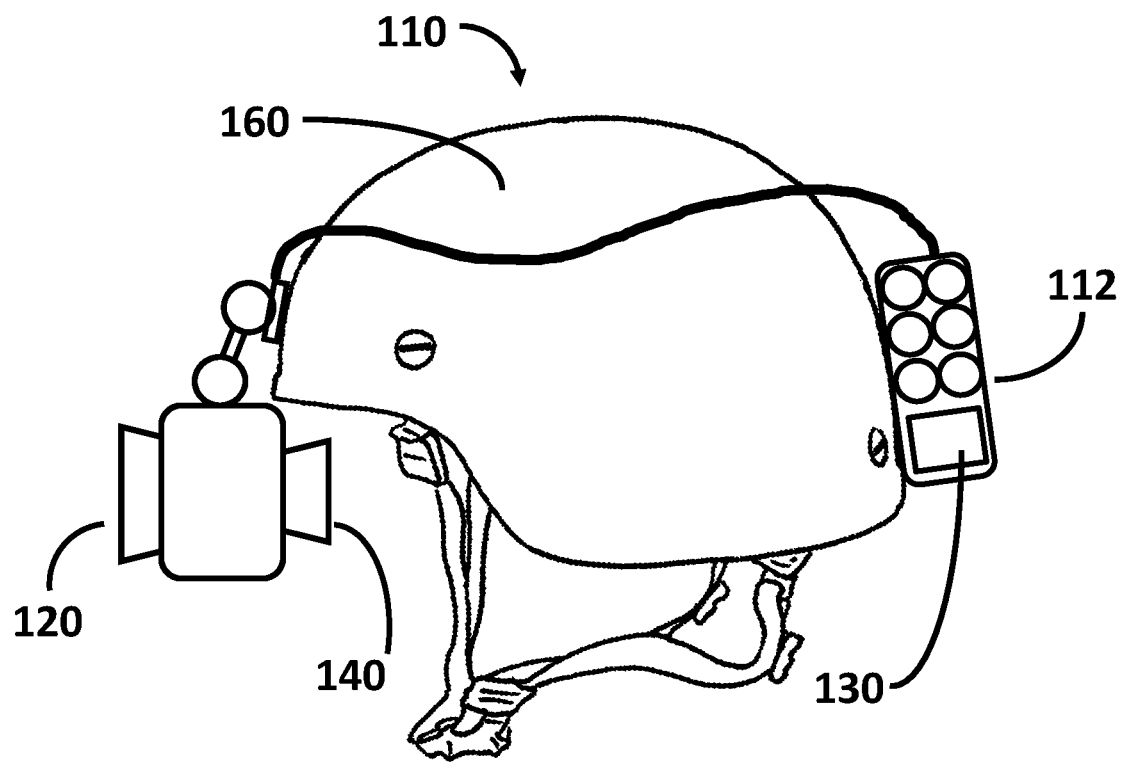
FIG. 5 illustrates an embodiment of the present invention mounted on a helmet.

In one embodiment (shown in FIG. 5), VLFRC 110 may be mounted on helmet 160. In other embodiments, VLFRC 110 may be mounted in a vehicle, or be held by or mounted to the body of a user that may be moving.

Figure 3:
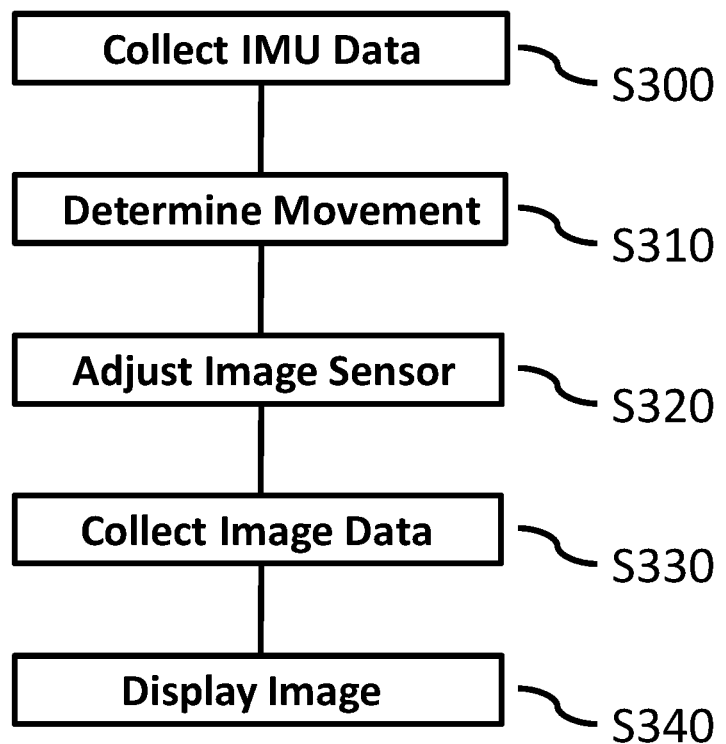
FIG. 3 illustrates a first flow chart showing processes performed by the present invention.

FIG. 3 illustrates a flow chart for the first embodiment of the present invention. In Step S300, IMU data is collected. The amount of motion of the system is determined in Step S310. The parameters of the image sensor are adjusted in Step S320, such as the frame rate and/or the latency time. Image data is collected in Step S330, and that data is displayed in Step S340.

Figure 4:
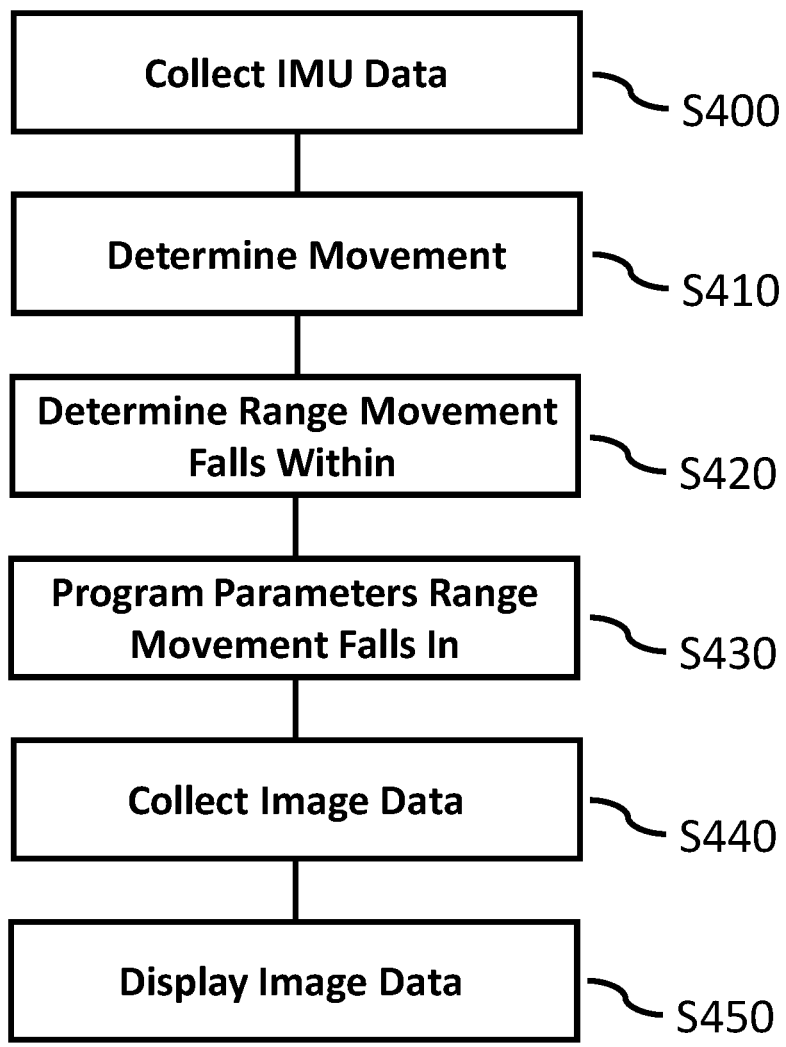
FIG. 4 illustrates a second flow chart showing processes performed by the present invention.

FIG. 4 provides a flow chart for the processing of VLFRC 110. In this embodiment, IMU data is collected in Step S400. Movement of the system is determined in Step S410. In Step S420, the amount of movement is determined to be within one of a set of predetermined ranges, each range being associated with a set of device parameters. In Step S430, the parameters for the range corresponding to the measured movement are used to program the VLFRC 110. Image data is then collected in Step S440, and displayed in Step S450. Possible exemplary ways of performing these steps are described hereinafter.

Pre-determined settings optimal for a given performance requirement at each camera frame rate are stored in VLFRC flash memory and user selection is loaded as default upon a power up cycle. Typical usage requires interfacing with a computer to implement changes to any of the camera settings stored in a temporary memory location and not committed to permanent changes, therefore not affecting the default configuration settings.

Integration of the IMU module, and inclusion of four presets of low and high angular velocity values, allows for monitoring of roll (X), pitch (Y), and yaw (Z) rate data, corresponding to motion of a user wearing the helmet. Upon an increase in any of the three values which go above a preset threshold and falls within one of four low/high ranges, the VLFRC FPGA adjusts first the exposure mode to eliminate or minimize any image blooming or saturation caused by a sudden change in image brightness in the observed scene, and then adjusts the image frame rate to 30 fps (frames per second) if at the 15 fps frame rate.

The FPGA sets the exposure mode in the following manner. Hereinafter, the two exposure modes will be referred to as Automatic and Manual. In Automatic mode, an Automatic Gain Control (AGC) circuit is activated. As noted above, this will eliminate or minimize any image blooming or saturation caused by a sudden change in image brightness in the observed scene, as well as compensate for lower integration times at higher frame rates. However, running the AGC circuit requires more power. Thus, at low frame rates, the FPGA sets the exposure mode to Manual, which shuts off the AGC circuit to reduce power consumption.

If angular velocity values fall into the second low/high range, the FPGA ensures the status of the exposure mode setting changing it again if needed, then executes a frame rate increase to 60 fps, and drops the latency to a lower value to minimize a portion of the delay of image frame build to user eyepiece display.

If angular velocity values fall into the third low/high range, the FPGA ensures the status of the exposure mode setting changing it again if needed, then executes a frame rate increase to 90 fps, and drops the latency to a lower value to further minimize the delay of image frame build to user eyepiece display.

The fourth monitored range when exceeded also causes the FPGA to ensure the status of the exposure mode setting changing it again if needed, then executes a frame rate increase to 120 fps, and drops the latency to its lowest allowed value further minimizing the delay of image frame build to user eyepiece display.

The firmware architecture allows the FPGA to execute any range at any time when motion is detected, without the need to step through any lower frame rate and latency values prior to the one being executed.

To minimize power consumption due to high frame rates and low latency values, the FPGA range monitoring is also allowed to reduce the frame rates and increase the latency, with the end goal of reaching 15 fps frame rate and a latency value of 150 ms or more, which is where the camera has the highest sensitivity in image detail. The lower frame rate and higher latency are also critical for extended battery life (when the VLFRC is operating from a battery) since higher frame rates and lower latency are directly proportional to clock rates, and a higher clock rate requires more power to maintain.

The reduction of frame rate and latency are accomplished in a different manner. The last selected frame rate and latency values are maintained for a preselected amount of time before the FPGA checks on the angular velocities to see where they fall within one of the other ranges. If the angular velocities do fall within a lower range, the FPGA will down select to a lower frame rate appropriate for the current user motion. Once the frame rate is either at 30 fps or 15 fps, the FPGA will then change the exposure mode back to Manual.

If while down selecting to a slower frame rate the IMU has a sudden increase in angular velocities, the FPGA will adjust the frame rate higher and latency lower if the angular velocities fall within another low/high range other than the one currently within.

Any new event will execute upon completion of the previous command set already executing in the FPGA, micro controller, or image sensor.

The invention will best be understood by first describing the typical usage before addition of the IMU. The user would power up the VLFRC already mounted on a helmet. The camera would power on at the previously programmed frame rate, which includes pre-programmed optimized default settings for ADCgain, PGAgain, and Column. ADCgain is the gain value for the Analog to Digital Converter (ADC) located in the image sensor. PGAgain is the gain value for the programmable gain amplifier also located in the image sensor. Column value sets the optimization for column non-uniformities in the image sensor image stream. All three values change with each of the programmed frame rates of 15, 30, 60, 90, and 120 fps, due to being optimized at each frame rate to meet a particular image performance requirement in the lab.

The user now has a streaming image appearing in the display in front of one eye, and if the user goes into motion, even very slight movements in azimuth or elevation, the image will have varying degrees of image tearing/smearing, delay, and/or latency depending on rotational velocity and direction of motion. If another frame rate is desired, the user would need to have a laptop or desktop computer along with control software tools to interface to the VLFRC and modify the default configuration to their desired settings.

This camera and display builds an image line by line in a typical format known as Progressive Scan, resulting in an image frame which is highly susceptible to camera motion creating image tearing and other motion artifacts when moved at a pace faster than the electronics and progressive scan rate can refresh the image frame. By running this camera at very high frame rates, 120 fps in this case, image tearing is minimized or eliminated depending on angular velocity. However, running a camera at such high frame rates requires higher image processing speeds resulting in higher power consumption, which in turn defeats the requirements to run in a low power consumption condition.

A programmed low frame rate setting between 15 fps or 30 fps and latency set above 100 ms are the driving causes for image tearing when the camera goes into motion. Typically, if the user knew he was going to be moving fast with the camera, he would want to program the camera to the higher frame rate of 120 fps, with a lower latency value between 10 ms and 2 ms, and the exposure mode set to Automatic. These settings provide the best operational settings for minimizing image tearing/smearing and motion sickness while on the move. However, if operating off of battery power, these settings may require that replacement batteries be on hand.

By running the VLFRC at 15 fps, it allows the camera pixels more dwell time to charge up to a higher level, increasing the sensitivity to changes in light, but the operational tradeoff is high image tearing/smearing and potential motion sickness for most users. Conversely, by running at 120 fps and low latency values, light sensitivity is reduced, and there's less potential for motion sickness, as well as greater power consumption.

By introducing the IMU roll (X), pitch (Y), and yaw (Z) angular velocities and motion monitoring, this allows for monitoring when the camera is at rest, where X, Y, and Z are below a programmed threshold values which allows for ignoring of random noise of 0.02 m/s (1σ RMS) as measured in the lab during development and testing, or when in motion, and where each axis is monitored by applying the axis data thru the following threshold conditions:

Is $(X_{low1} \leq X \leq X_{high1})$ or $(Y_{low1} \leq Y \leq Y_{high1})$ or $(Z_{low1} \leq Z \leq Z_{high1})$?

Is $(X_{low2} \leq X \leq X_{high2})$ or $(Y_{low2} \leq Y \leq Y_{high2})$ or $(Z_{low2} \leq Z \leq Z_{high2})$?

Is $(X_{low3} \leq X \leq X_{high3})$ or $(Y_{low3} \leq Y \leq Y_{high3})$ or $(Z_{low3} \leq Z \leq Z_{high3})$?

Is $(X \text{ or } Y \text{ or } Z) \geq H_{AV}$?

The final condition looks for an axis value exceeding a programmed threshold indicating high angular velocities, which then results in a frame rate change to 120 fps along with minimizing the latency value, and ensuring the VLFRC exposure mode is set to Automatic.

Once the VLFRC has been changed to a faster frame rate and lower latency times, the IMU and FPGA continue to monitor for additional changes in angular velocities, such as another increase in velocity, for which the VLFRC will adjust to a higher frame rate if another threshold is reached.

Additionally the IMU and FPGA monitor for a decrease in angular velocity. When a decrease is seen, the IMU and FPGA now monitors elapsed time to see if a time threshold has been met for a maintained reduction in angular velocity. Once the programmed time threshold has been reached, then the IMU and FPGA continues to monitor for an increase or decrease in angular velocities, and if a lower threshold is met then another reduction of frame rate will occur by first ensuring the VLFRC Exposure Mode is set to Automatic, the frame rate will be slowed down one step, and the latency appropriately adjusted to a larger value. The IMU and FPGA will continue to monitor for another decrease or increase in angular velocities. If another decrease has occurred which crosses the next threshold, then the IMU and FPGA will execute another frame rate reduction in speed along with an appropriate latency value. If the user has stopped moving, the IMU and FPGA will continue to do frame rate reductions until the frame rate reaches 15 fps, at which time the user has come to rest.

The present written description uses examples to disclose the present subject matter, including the best mode, and also to enable any person skilled in the art to practice the present subject matter, including making and using any devices or systems and performing any incorporated and/or associated methods. While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An imaging and display system comprising:
   an image sensor configured to controllably detect images and collect image data;
   an inertial measurement unit configured to measure movement of the system and provide multi-axis angular velocity data;
   a display unit configured to controllably display an image stream of the image data; and
   a control unit configured to control the image sensor and the display of image stream by the display unit in real-time based on a method of imaging and display using the multi-axis angular velocity data from the inertial measurement unit, said method of imaging and display comprising the steps of:
      collecting the multi-axis angular velocity data from the inertial measurement unit to the control unit,
      determining an amount of motion by the control unit based on the multi-axis angular velocity data,
      adjusting device parameters of the image sensor based on the determined amount of motion by the control unit,
      collecting image data from said image sensor, and
      displaying the image stream by the display unit based on the collected image data.

2. The imaging and display system according to claim 1, wherein said image sensor detects visible light to output image data.

3. The imaging and display system according to claim 1, wherein said image sensor outputs image data based on at least one of near infrared, short wave IR, mid wave IR, and long wave IR detection.

4. The imaging and display system according to claim 1, wherein the control unit is configured to control a frame rate of the image sensor and the display unit.

5. The imaging and display system according to claim 1, wherein the control unit adjusts at least one of a frame rate of the image sensor and the display unit, and a latency time of the display unit.

6. The imaging and display system according to claim 1, wherein said inertial measurement unit provides multi-axis angular velocity data indicative of roll, pitch, and yaw rates.

7. The imaging and display system according to claim 1, wherein said device parameters are at least one of frame rate and latency time.

8. A variable latency and frame rate camera system comprising:
- a battery pack with a user button capable of powering up the variable latency and frame rate camera system;
- an inertial measurement unit configured to measure movement of the system and provide angular velocity data;
- a control unit to receive said angular velocity data and configure a configuration data set to minimize motion artifacts based on an imaging and display method using a determined angular velocity status in real time;
- an image sensor configured according to said configuration data set to produce a resulting image stream; and
- a display unit to receive the resulting image stream and controllably display the resulting image stream for eye level display with minimal motion artifacts, wherein said imaging and display method comprises the steps of:
  - collecting inertial measurement unit data from the inertial measurement unit to the control unit,
  - determining a measured movement of the system as an amount of movement by the control unit,
  - determining by the control unit whether the amount of movement is within one of a set of predetermined ranges, each range being associated with a set of device parameters,
  - programming by the control unit a set of device parameters corresponding to the measured movement,
  - collecting image data from said image sensor according to the device parameters as set by the control unit, and
  - displaying a resulting image stream by the display unit based on the collected image data.

9. The variable latency and frame rate camera system according to claim 8, wherein said display unit is a micro display and eyepiece for eye level display.

10. The variable latency and frame rate camera system according to claim 8, wherein said control unit includes a field programmable gate array and micro controller assembly which initializes said image sensor with a timing configuration data.

11. The variable latency and frame rate camera system according to claim 8, wherein said control unit monitors angular velocities, and depending on a determined angular velocity status, said control unit configures said configuration data set to change a frame rate.

12. The variable latency and frame rate camera system according to claim 8, wherein said inertial measurement unit outputs angular velocity data to said control unit for monitoring of multi-axis angular velocities.

13. The variable latency and frame rate camera system according to claim 8, wherein said variable latency and frame rate camera system is capable of adjusting at least one of multiple frame rates, a latency adjustment, exposure mode, manual gain, and manual level, wherein default values can be set to help reduce power consumption.

14. The variable latency and frame rate camera system according to claim 8, wherein said imaging and display system can be hand held, mounted in a vehicle, worn on a body under movement, and/or helmet mountable.

15. The variable latency and frame rate camera system according to claim 8, wherein four presets of low and high angular velocity values allow for monitoring of roll, pitch, and yaw rate data.

16. The variable latency and frame rate camera system according to claim 8, wherein pre-determined settings optimal for a given performance requirement at each camera frame rate are stored in a flash memory for user selection.

17. The variable latency and frame rate camera system according to claim 8, wherein four presets of low and high angular velocity values allow for monitoring of roll, pitch, and yaw rate data from the collection of inertial measurement unit data.

18. The variable latency and frame rate camera system according to claim 8, wherein said determining a measured movement of the system is based on roll, pitch, and yaw rate data collected from the inertial measurement unit.

* * * * *